United States Patent
Sun et al.

(10) Patent No.: US 9,296,669 B2
(45) Date of Patent: Mar. 29, 2016

(54) PROCESS FOR REACTOR PASSIVATION

(71) Applicant: E.I. DU PONT DE NEMOURS AND COMPANY, Wilmington, DE (US)

(72) Inventors: Xuehui Sun, Swedesboro, NJ (US); Mario Joseph Nappa, Newark, DE (US); Haiyou Wang, Amherst, NY (US); Haluk Kopkalli, Staten Island, NY (US)

(73) Assignee: E.I. DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/371,069

(22) PCT Filed: Jan. 8, 2013

(86) PCT No.: PCT/US2013/020632
§ 371 (c)(1),
(2) Date: Jul. 8, 2014

(87) PCT Pub. No.: WO2013/106305
PCT Pub. Date: Jul. 18, 2013

(65) Prior Publication Data
US 2014/0364657 A1 Dec. 11, 2014

Related U.S. Application Data

(60) Provisional application No. 61/584,496, filed on Jan. 9, 2012.

(51) Int. Cl.
- C07C 17/25 (2006.01)
- B01J 19/00 (2006.01)
- B01J 19/02 (2006.01)
- B01J 19/24 (2006.01)

(52) U.S. Cl.
CPC .............. *C07C 17/25* (2013.01); *B01J 19/002* (2013.01); *B01J 19/02* (2013.01); *B01J 19/24* (2013.01); *B01J 19/2415* (2013.01); *B01J 2219/00247* (2013.01); *B01J 2219/0236* (2013.01); *B01J 2219/0277* (2013.01); *B01J 2219/0286* (2013.01)

(58) Field of Classification Search
CPC ......... C07C 17/25; B01J 19/002; B01J 19/02; B01J 19/24; B01J 19/2415; B01J 2219/0236; B01J 2219/0286; B01J 2219/00247; B01J 2219/0277
USPC ....................................................... 570/155
See application file for complete search history.

(56) References Cited

U.S. PATENT DOCUMENTS

| | | | |
|---|---|---|---|
| 7,230,146 B2 * | 6/2007 | Merkel et al. | 570/155 |
| 7,795,481 B2 * | 9/2010 | Nappa et al. | 570/155 |
| 8,217,124 B2 * | 7/2012 | Littmann et al. | 526/64 |
| 8,399,721 B2 * | 3/2013 | Nappa et al. | 570/176 |
| 8,445,735 B2 | 5/2013 | Nappa | |
| 8,846,990 B2 * | 9/2014 | Wang et al. | 570/155 |
| 2010/0048837 A1 * | 2/2010 | Martin et al. | 526/64 |
| 2011/0031436 A1 | 2/2011 | Mahler et al. | |
| 2013/0338408 A1 | 12/2013 | Merkel et al. | |
| 2014/0350309 A1 | 11/2014 | Wang et al. | |

OTHER PUBLICATIONS

Office Action dated Apr. 21, 2015 received from the Chinese Patent Office from related Chinese Patent Application No. 201380005117.2.
Urbano, F.J., et al., "Hydrogenolysis of organohalogen compounds over palladium supported catalysts"; Journal of Molecular Catalysis A: Chemical, 2001, vol. 173, pp. 329-345.
International Search Report dated Apr. 23, 2013 corresponding to PCT/US2013/020632.
European Search Report dated Jul. 10, 2015 corresponding to EP13736426.1.

* cited by examiner

*Primary Examiner* — Shailendra Kumar
(74) *Attorney, Agent, or Firm* — Scully, Scott, Murphy & Presser; Richard Catania

(57) ABSTRACT

Disclosed is a process for passivating a surface of a dehydrochlorination reactor comprising: stopping a flow of hydrochlorofluoropropane to a reactor, passing a gas mixture comprising hydrogen gas through the reactor at a temperature of at least 25° C. for a period of time sufficient to restore the selectivity of a dehydrochlorination reaction, stopping the flow of the hydrogen gas mixture, and resuming the flow of hydrochlorofluoropropane to the dehydrochlorination reaction. Also disclosed is a process for producing a fluoropropene of formula $CF_3CX=CX_2$, wherein each X is F or H, at least one X is H and at least one X is F, comprising pyrolyzing a hydrochlorofluoropropane of formula $CF_3CXYCX_2Y$, wherein each X is F or H, at least one X is H, and at least one X is F and one Y is Cl and the other Y is H, in the gas-phase in the absence of a catalyst in a reaction vessel, maintained at a temperature high enough to effect the pyrolysis of said hydrochlorofluoropropane to said fluoropropene, and wherein said reaction vessel is periodically subjected to a passivation step to passivate the inner surface of said reaction vessel. Also disclosed is a process for producing a fluoropropene of formula $CF_3CX=CX_2$, wherein each X is F or H, at least one X is H and at least one X is F, comprising pyrolyzing a hydrochlorofluoropropane of formula $CF_3CXYCX_2Y$, wherein each X is F or H, at least one X is H, and at least one X is F and one Y is Cl and the other Y is H, in the gas-phase in the absence of a catalyst in a reaction vessel, maintained at a temperature high enough to effect the pyrolysis of said hydrochlorofluoropropane to said fluoropropene, and wherein said hydrochlorofluoropropane comprises less than 300 ppm of hydrogen fluoride.

21 Claims, No Drawings

PROCESS FOR REACTOR PASSIVATION

CROSS-REFERENCE TO RELATED APPLICATIONS

This application is a '371 of PCT Application No. PCT/US2013/020632, which was filed on Jan. 8, 2013 and claims priority of U.S. provisional application U.S. Ser. No. 61/584,496, which was filed on Jan. 9, 2012, the entire contents of both of which are incorporated herein by reference.

BACKGROUND INFORMATION

1. Field of the Disclosure

This disclosure relates in general to methods of synthesis of fluorinated olefins.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential.

SUMMARY

In one embodiment, disclosed is a process for passivating a surface of a dehydrochlorination reactor comprising: stopping a flow of hydrochlorofluoropropane to a reactor, passing a gas mixture comprising hydrogen gas through the reactor at a temperature of at least 25° C. for a period of time sufficient to restore the selectivity of a dehydrochlorination reaction, stopping the flow of the hydrogen gas mixture, and resuming the flow of hydrochlorofluoropropane to the dehydrochlorination reaction.

In another embodiment, disclosed is a process for producing a fluoropropene of formula $CF_3CX=CX_2$, wherein each X is F or H, at least one X is H and at least one X is F, comprising: pyrolyzing a hydrochlorofluoropropane of formula $CF_3CXYCX_2Y$, wherein each X is F or H, at least one X is H, and at least one X is F and one Y is Cl and the other Y is H, in the gas-phase in the absence of a catalyst in a reaction vessel, maintained at a temperature high enough to effect the pyrolysis of said hydrochlorofluoropropane to said fluoropropene, and wherein said reaction vessel is periodically subjected to a passivation step to passivate the inner surface of said reaction vessel.

In yet another embodiment, disclosed is a process for producing a fluoropropene of formula $CF_3CX=CX_2$, wherein each X is F or H, at least one X is H and at least one X is F, comprising: pyrolyzing a hydrochlorofluoropropane of formula $CF_3CXYCX_2Y$, wherein each X is F or H, at least one X is H, and at least one X is F and one Y is Cl and the other Y is H, in the gas-phase in the absence of a catalyst in a reaction vessel, maintained at a temperature high enough to effect the pyrolysis of said hydrochlorofluoropropane to said fluoropropene, and wherein said hydrochlorofluoropropane comprises less than 300 ppm of hydrogen fluoride.

The foregoing general description and the following detailed description are exemplary and explanatory only and are not restrictive of the invention, as defined in the appended claims.

DETAILED DESCRIPTION

In one embodiment, disclosed is a process for passivating a surface of a dehydrochlorination reactor comprising: stopping a flow of hydrochlorofluoropropane to a reactor, passing a gas mixture comprising hydrogen gas through the reactor at a temperature of at least 25° C. for a period of time sufficient to restore the selectivity of a dehydrochlorination reaction, stopping the flow of the hydrogen gas mixture, and resuming the flow of hydrochlorofluoropropane to the dehydrochlorination reaction.

In another embodiment, disclosed is a process for producing a fluoropropene of formula $CF_3CX=CX_2$, wherein each X is F or H, at least one X is H and at least one X is F, comprising: pyrolyzing a hydrochlorofluoropropane of formula $CF_3CXYCX_2Y$, wherein each X is F or H, at least one X is H, and at least one X is F and one Y is Cl and the other Y is H, in the gas-phase in the absence of a catalyst in a reaction vessel, maintained at a temperature high enough to effect the pyrolysis of said hydrochlorofluoropropane to said fluoropropene, and wherein said reaction vessel is periodically subjected to a passivation step to passivate the inner surface of said reaction vessel.

In yet another embodiment, disclosed is a process for producing a fluoropropene of formula $CF_3CX=CX_2$, wherein each X is F or H, at least one X is H and at least one X is F, comprising: pyrolyzing a hydrochlorofluoropropane of formula $CF_3CXYCX_2Y$, wherein each X is F or H, at least one X is H, and at least one X is F and one Y is Cl and the other Y is H, in the gas-phase in the absence of a catalyst in a reaction vessel, maintained at a temperature high enough to effect the pyrolysis of said hydrochlorofluoropropane to said fluoropropene, and wherein said hydrochlorofluoropropane comprises less than 300 ppm of hydrogen fluoride.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Before addressing details of embodiments described below, some terms are defined or clarified.

As used herein, the terms "pyrolyzing" and "pyrolysis" refer to the decomposition or breaking down of a material or compound due to heat in the absence of oxygen or any other reagents.

As used herein, the term in the "absence of a catalyst" means that no material, compound or substance is added to the pyrolysis reactor that increases the reaction rate by reducing the activation energy of the pyrolysis process. More specifically, absence of a catalyst means the absence of conventional catalysts having high surface area in a particulate, pellet, fibrous or supported form that are useful in promoting the elimination of hydrogen chloride from a hydrochlorofluorocarbon (I.e. dehydrochlorination).

As used herein, "reaction vessel" refers to any vessel in which the reaction may be performed in either a batchwise mode, or in a continuous mode. Suitable vessels include batch reactor vessels, or tubular reactors.

In one embodiment, the reaction vessel is comprised of materials which are resistant to corrosion including stainless steel, Hastelloy, Inconel, Monel, gold, or gold-lined or quartz.

As used herein, "percent selectivity" is defined as the weight of a desired product formed, as a fraction of the total amount of the products formed in the reaction, and excluding the starting chlorofluorocarbon.

As used herein, "restoring the selectivity" of a dehydrochlorination reaction refers to passivating an interior surface of a reactor to remove metal fluorides and/or chlorides to reduce the amount of dehydrofluorination product formed in the dehydrohalogenation of a hydrochlorofluoropropane relative to the amount of dehydrochlorination product formed.

As used herein, "periodically subjected" to a passivation step refers to, at some interval, subjecting the interior of a dehydrochlorination reactor to a passivation step, as disclosed herein, the frequency of which step correlates with the concentration of impurities in the hydrochlorofluorocarbon reactor feed which cause the formation of metal fluorides and/or chlorides on the interior surfaces of said reactor.

As used herein, "percent conversion" is defined as 100%, less the weight percent of starting hydrochlorofluoropropane in the effluent from the reaction vessel. As used herein, "percent selectivity" is defined as the amount of dehydrochlorination product formed, divided by the amount of hydrochlorofluoropropane consumed. By way of illustration, in the dehydrochlorination of 244bb, the selectivity is the amount of 1234yf produced divided by the amount of 1234yf plus the net amount of 1233xf plus other impurities produced.

The hydrochlorofluoropropane described herein has the formula $CF_3CXYCX_2Y$, wherein each X is F or H, at least one X is H, and at least one X is F, and one Y is Cl and the other Y is H. A fluoropropene as described herein has the formula $CF_3CX=CX_2$ wherein each X is F or H, at least one X is H, and at least one X is F. Representative hydrochlorofluoropropanes include 1,1,1,2-tetrafluoro-2-chloropropane, 1,1,1,2-tetrafluoro-3-chloropropane, 1,1,1,3-tetrafluoro-2-chloropropane, 1,1,1,3-tetrafluoro-3-chloropropane, 1,1,1,2,3-pentafluoro-2-chloropropane, 1,1,1,2,3-pentafluoro-3-chloropropane, 1,1,1,3,3-pentafluoro-2-chloropropane and 1,1,1,3,3-pentafluoro-3-chloropropane.

Representative fluoropropenes include 2,3,3,3-tetrafluoropropene, 1,3,3,3-tetrafluoropropene, 1,2,3,3,3-pentafluoropropene and 1,1,3,3,3-pentafluoropropene.

In one embodiment, the hydrochlorofluoropropane is 1,1,1,2-tetrafluoro-2-chloropropane and the fluoropropene is 2,3,3,3-tetrafluoropropene. In another embodiment, the hydrochlorofluoropropane is 1,1,1,2-tetrafluoro-3-chloropropane and the fluoropropene is 2,3,3,3-tetrafluoropropene. In yet another embodiment, the hydrochlorofluoropropane is 1,1,1,3-tetrafluoro-2-chloropropane and the fluoropropene is 1,3,3,3-tetrafluoropropene. In yet another embodiment, the hydrochlorofluoropropane is 1,1,1,3-tetrafluoro-3-chloropropane and the fluoropropene is 1,3,3,3-tetrafluoropropene. In yet another embodiment, the hydrochlorofluoropropane is 1,1,1,2,3-pentafluoro-2-chloropropane and the fluoropropene is 1,2,3,3,3-pentafluoropropene. In yet another embodiment, the hydrochlorofluoropropane is 1,1,1,2,3-pentafluoro-3-chloropropane and the fluoropropene is 1,2,3,3,3-pentafluoropropene. In yet another embodiment, the hydrochlorofluoropropane is 1,1,1,3,3-pentafluoro-2-chloropropane and the fluoropropene is 1,1,3,3,3-pentafluoropropene. In yet another embodiment, the hydrochlorofluoropropane is 1,1,1,3,3-pentafluoro-3-chloropropane and the fluoropropene is 1,1,3,3,3-pentafluoropropene.

In one embodiment, fluoropropenes are prepared by thermal dehydrochlorination of hydrochlorofluoropropanes. This reaction occurs selectively, in the absence of a catalyst. In one embodiment, a hydrochlorofluoropropane is introduced into a reaction vessel wherein the temperature is maintained at a temperature high enough to effect the thermal dehydrochlorination of the hydrochlorofluoropropane. In one embodiment, the temperature is high enough to effect the thermal dehydrochlorination of the hydrochlorofluoropropane to a percent conversion of at least 10%. In another embodiment, the temperature is high enough to effect the thermal dehydrochlorination of the hydrochlorofluoropropane to a percent conversion of at least 30%. In yet another embodiment, the temperature is high enough to effect the thermal dehydrochlorination of the hydrochlorofluoropropane to a percent conversion of at least 50%. In yet another embodiment, the temperature is high enough to effect the thermal dehydrochlorination of the hydrochlorofluoropropane to a percent conversion of at least 80%. In yet another embodiment, the temperature is high enough to effect the thermal dehydrochlorination of the hydrochlorofluoropropane to a percent conversion of at least 70% for at least 12 hours of continuous operation.

In one embodiment, the hydrochlorofluoropropane is introduced into a reaction vessel wherein the temperature is maintained at a temperature in the range of from about 200° C. to about 700° C. In another embodiment, the temperature of the reaction vessel is maintained in the range from about 300° C. to about 650° C. In yet another embodiment, the temperature of the reaction vessel is maintained at a temperature high enough to effect the pyrolysis of the hydrochlorofluoropropane to fluoropropene with a selectivity of 80% or greater. In yet another embodiment, the temperature of the reaction vessel is maintained at a temperature high enough to effect the pyrolysis of the hydrochlorofluoropropane to the fluoropropene with a selectivity of 85% or greater. In yet another embodiment, the temperature of the reaction vessel is maintained at a temperature high enough to effect the pyrolysis of the hydrochlorofluoropropane to fluoropropene with a selectivity of 90% or greater.

In one embodiment, the reaction vessel is comprised of materials which are resistant to corrosion. In one embodiment, these materials comprise alloys, such as stainless steel, Hastelloy, Inconel, Monel, and gold, gold-lined or quartz.

In one embodiment, the hydrochlorofluoropropane is preheated in a vaporizer to a temperature of from about 30° C. to about 100° C. In another embodiment, the hydrochlorofluoropropane is preheated in a vaporizer to a temperature of from about 30° C. to about 80° C.

In some embodiments, an inert diluent gas is used as a carrier gas for the hydrochlorofluoropropane. In one embodiment, the carrier gas is selected from nitrogen, argon, helium or carbon dioxide and mixtures thereof.

In some embodiments, the selectivity of the thermal dehydrochlorination reaction declines over time. In some embodiments, the rate of this change in selectivity is dependent upon the purity of the hydrochlorofluorocarbon feed material. Without wishing to be bound by any particular theory, applicants have come to believe that changes in the selectivity of the thermal dehydrochlorination reaction arise as interior surfaces of the pyrolysis reactor become halogenated. In particular, changes in the selectivity of the thermal dehydrochlorination reaction may arise as interior surfaces of the pyrolysis reactor become fluorinated.

In some embodiments, this change in selectivity of the thermal dehydrochlorination reaction can occur after 60 hours of operation. In some embodiments, this change in selectivity of the thermal dehydrochlorination reaction can occur after 2000 hours of operation.

In some embodiments, the presence of impurities in the hydrochlorofluorocarbon feedstock can significantly accelerate the rate at which this loss of selectivity occurs. One common impurity which can be present in 2-choro-1,1,2-tetrafluoropropane (244bb) is residual hydrogen fluoride.

In one embodiment of the thermal dehydrochlorination of HCFC-244bb, the HCFC-244bb feedstock comprises less than 300 ppm hydrogen fluoride as an impurity. In another embodiment, the HCFC-244bb feedstock comprises less than 200 ppm hydrogen fluoride as an impurity. In yet another embodiment, the HCFC-244bb feedstock comprises less than 100 ppm hydrogen fluoride as an impurity.

In some embodiments, the selectivity of a thermal dehydrochlorination reaction can be increased by passivating the surfaces of the interior of the reactor. This can be accomplished by passing a gas comprising hydrogen through the reactor. In some embodiments, the flow of hydrochlorofluorocarbon being fed to the reactor for dehydrochlorination is stopped prior to or essentially simultaneously with the introduction of the hydrogen comprising gas. In some embodiments, the flow of hydrochlorofluorocarbon being fed to the reactor for dehydrochlorination is not interrupted during the passivating process.

In some embodiments, the gas comprising hydrogen is 100% hydrogen. In some embodiments, the gas comprising hydrogen is a mixture of hydrogen and an inert diluent gas. In some embodiments, the inert diluent gas is nitrogen, helium, argon or neon and mixtures thereof. In additional embodiments, reducing agents other than hydrogen may be employed. Such reducing agents include, without limitation, $NH_3$ (ammonia), CO (carbon monoxide), $CH_4$ (methane); mixtures of these, including mixtures with hydrogen, may also be used. These reducing agents can further be mixed with an inert diluent gas as above, e.g. in one embodiment, a mixture of ammonia and nitrogen is used. In one practice, ammonia acts as a reducing agent, as is; in another embodiment, ammonia is a source of hydrogen for passivation, as suggested by its decomposition temperature (about 450° to about 500° C.) and its initiation temperature (about 430° C.). In some embodiments, the gas contains from 0.5 mole percent to 100 mole percent hydrogen. In some embodiments the gas comprises from 0.5 mole percent to 30 mole percent hydrogen. In some embodiments, the gas comprises from 3 to 30 mole percent hydrogen. The length of time necessary to passivate the surfaces of the reactor for the thermal dehydrochlorination reaction varies inversely with the amount of hydrogen in the gas mixture comprising hydrogen. Lower concentrations will necessarily require longer times to passivate the reactor surfaces. Higher concentrations will complete the passivation process and increase the selectivity of the dehydrochlorination reaction in a shorter time.

In some embodiments, the passivation process can be conducted at a temperature from about 25° C. to about 600° C. In some embodiments, the passivation process can be conducted at a temperature from 200° C. to 500° C. In some embodiments, the passivation process is conducted at a temperature of from about 400° C. to about 500° C. In another embodiment, the passivation process is conducted at the same temperature as the dehydrochlorination process, so as to not have to change the temperature set point of the reactor.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Legend
HFC-244bb is 2-chloro-1,1,1,2-tetrafluoropropane
HFO-1234yf is 2,3,3,3-tetrafluoropropene
HCFO-1233xf is 2-chloro-3,3,3-trifluoropropene Example 1

Example 1 shows the conversion of 2-chloro-1,1,1,2-tetrafluoropropane to 2,3,3,3-tetrafluoropropene in the absence of a catalyst at 480° C.

A mixture of 99% of 244bb and 1% of 1233xf was passed through a ½"×12" (ID 0.334") Inconel 625 tube with flow rates of 2.4 ml/hr, 1.2 ml/hr, 0.8 ml/hr and 0.4 ml/hr at 480° C. at 1 atmosphere pressure. The stream from the reactor was analyzed by GC and GC-MS. The result of the test is listed in Table 1 below. The reaction shows high selectivity to 1234yf and low selectivity to 1233xf.

TABLE 1

| | Flow rate | | | |
|---|---|---|---|---|
| | 2.4 ml/hr | 1.2 ml/hr | 0.8 ml/hr | 0.4 ml/hr |
| % 1234yf | 22 | 31 | 38 | 51 |
| % 244bb | 76 | 67 | 59 | 47 |
| % 1233xf | 1 | 1 | 1 | 1 |

Example 2

Example 2 shows the effect of a reactor surface which has been treated with oxygen and HF on the selectivity of the dehydrohalogenation reaction.

The reactor in Example 1 was treated with 10% $O_2$ at 480 C for 1 hr and then 50% HF at 480 C for 2 hr. Then the mix of 99% of 244bb and 1% of 1233xf was passed through a ½"× 12" (ID 0.334") Inconel 625 tube with flow rate 1.2 ml/hr, 0.8 ml/hr and 0.4 ml/hr at 480° C. at 1 atmosphere pressure. The stream from the reactor was analyzed by GC and GC-MS. The result of the test is listed in Table 2 below. The reaction shows low selectivity to 1234yf and high selectivity to 1233xf.

TABLE 2

| | Flow rate | | |
|---|---|---|---|
| | 1.2 ml/hr | 0.8 ml/hr | 0.4 ml/hr |
| % 1234yf | 7 | 7 | 7 |
| % 244bb | 21 | 9 | 4 |
| % 1233xf | 71 | 83 | 88 |

Example 3

Example 3 shows the effect of passivating the reactor surface with 30% hydrogen gas.

The reactor in example 2 was reduced with 30% $H_2$ (balanced with $N_2$) at 480° C. for 12 hrs and then the mix of 99% of 244bb and 1% of 1233xf was passed through the reactor with flow rate 2.4 ml/hr, 1.2 ml/hr, 0.8 ml/hr and 0.4 ml/hr at 480° C. at 1 atmosphere pressure. The stream from the reactor was analyzed by GC and GC-MS. The result of the test is listed in Table 3 below. The reaction shows high selectivity to 1234yf and low selectivity to 1233xf after being treated with 30% $H_2$. The selectivity of reaction after reduction is equivalent to a brand new tube. The reactor was then operated for another 155 hours at 25 psig at 1 ml/hr flow rate without selectivity change. This data is summarized in Table 4.

TABLE 3

| | Flow rate | | | |
|---|---|---|---|---|
| | 2.4 ml/hr | 1.2 ml/hr | 0.8 ml/hr | 0.4 ml/hr |
| % 1234yf | 22 | 35 | 45 | 59 |
| % 244bb | 74 | 63 | 53 | 38 |
| % 1233xf | 1 | 1 | 1 | 1 |

TABLE 4

| Time (hr) | Temp (° C.) | % 1234yf | % 244bb | % 1233xf |
|---|---|---|---|---|
| 31 | 455 | 47.7 | 48.4 | 2.2 |
| 51 | 455 | 37.2 | 61.2 | 1.1 |
| 91 | 455 | 29.4 | 69.0 | 1.2 |
| 137 | 455 | 29.3 | 69.1 | 1.2 |
| 165 | 455 | 28.3 | 70.2 | 1.2 |
| 185 | 480 | 55.2 | 43.0 | 1.1 |

Example 4

Example 4 shows the effect of passivating the reactor surface with 3% hydrogen gas.

The reactor in example 2 was reduced with 3% hydrogen (balanced with nitrogen) at 480° C. for 36 hours at atmospheric pressure and then the mix of 99% of 244bb and 1% of 1233xf was passed through the reactor with flow rate 1.2 ml/hr, 0.8 ml/hr and 0.4 ml/hr at 450° C. and 480° C. at atmospheric pressure. The stream from the reactor was analyzed by GC and GC-MS. Results are summarized in Table 5 below.

TABLE 5

| Temp | % 1234yf | % 244bb | % 1233xf |
|---|---|---|---|
| 450 | 54 | 44 | 1 |
| 480 | 56 | 42 | 1 |

Example 5

Example 5 illustrates long reactor life in the dehydrochlorination of 244bb in the absence of hydrogen fluoride.

A mixture of 99% of 244bb and 1% of 1233xf was passed through a ½"×12" (ID 0.334") Inconel 625 tube for dehydrochlorination at a flow rate of 1 ml/hr. The 244bb used in this reaction was scrubbed by deionized water and contained no detectable HF. The stream from the reactor was analyzed by GC and GC-MS. The result of the test is listed in Table 6 below. The reaction shows high selectivity to 1234yf and low selectivity to 1233xf out to 2000 hours of operation.

TABLE 6

| Time (hr) | % 1234yf | % 1233xf | % 244bb | Temp (° C.) |
|---|---|---|---|---|
| 600 | 24.1 | 1.0 | 74.6 | 440 |
| 1500 | 29.0 | 1.1 | 69.5 | 445 |
| 2002 | 24.0 | 1.1 | 74.6 | 446 |

Example 6

Example 6 demonstrates a rapid decrease in selectivity after feed of 244bb with HF.

A mixture of 99% 244 bb and 1% of 1233xf was passed through a ½"×12" (ID 0.334") Inconel 625 tube at 1.2 ml/hr for dehydrochlorination. The data in Table 7 shows good selectivity to 1234yf and essentially no more 1233xf than is present in the feed. Then 3 sccm of HF was co-fed with the 244bb mixture for 19 hours. After the HF was stopped, the feed of 99% of 244bb and 1% of 1233xf continued for dehydrochlorination. The stream from the reactor was analyzed by GC and GC-MS. The result of the test is listed in Table 7, indicating increased amounts of 1233xf product.

TABLE 7

| | % 1234yf | % 244bb | %1233xf | Temp (° C.) |
|---|---|---|---|---|
| Time (hr) | | | | |
| 1 | 32.5% | 66.0% | 1.1% | 486 |
| 2 | 29.5% | 69.0% | 1.1% | 486 |
| 3 | 31.2% | 67.3% | 1.1% | 486 |
| 4 | 31.2% | 67.3% | 1.1% | 486 |
| After HF treatment | | | | |
| 2 | 29.4% | 66.1% | 3.6% | 459 |
| 4 | 28.8% | 66.7% | 3.7% | 476 |
| 6 | 28.1% | 67.1% | 3.9% | 483 |
| 8 | 27.6% | 67.4% | 4.1% | 485 |
| 10 | 28.0% | 66.6% | 4.3% | 485 |
| 12 | 28.7% | 65.7% | 4.4% | 482 |

TABLE 7-continued

|    | % 1234yf | % 244bb | %1233xf | Temp (° C.) |
|----|----------|---------|---------|-------------|
| 14 | 28.8%    | 65.4%   | 4.4%    | 477         |
| 16 | 29.4%    | 64.7%   | 4.4%    | 475         |

Example 7

Example 7 demonstrates rapid reduction in dehydrochlorination selectivity after exposure of a reactor to HF and oxygen.

A mix of 99% of 244bb and 1% of 1233xf was passed through a 1"×12" (ID 0.87") Inconel 625 tube with flow rate 1.2 ml/hr at 480 C at atmosphere pressure. The stream from the reactor was analyzed by GC and GC-MS every hour. The result of the test is listed in Table 8 below. The reaction shows high selectivity to 1234yf and low selectivity to 1233xf. Then the reactor was treated with 20% HF at 480 C for 1 hr and followed by 10% O2 for two hours. The mix of 99% of 244bb and 1% of 1233xf was fed into the reactor at 1 ml/hr at 480 C and the stream from the reactor was analyzed by GC-MS every hour.

TABLE 8

| GC shot | Mole Percents | | | | Furnace C. | Liquid ml/hr |
|---------|---------------|--------|--------|--------|----|------|
|         | 1234yf | 244bb | 1233xf | Others | | |
| New tube | | | | | | |
| 1 | 59.88% | 37.96% | 1.16% | 1.00% | 480 | 1.20 |
| 2 | 60.06% | 37.79% | 1.15% | 1.00% | 480 | 1.20 |
| 3 | 59.94% | 38.02% | 1.15% | 0.90% | 480 | 1.20 |
| 4 | 59.28% | 38.76% | 1.14% | 0.82% | 480 | 1.20 |
| Fluorinated and oxidized | | | | | | |
| 1 | 26.61% | 20.78% | 50.63% | 1.97% | 480 | 1.00 |
| 2 | 30.75% | 19.81% | 46.79% | 2.64% | 480 | 1.00 |
| 3 | 32.78% | 20.73% | 43.70% | 2.79% | 480 | 1.00 |
| 4 | 31.31% | 24.75% | 41.36% | 2.57% | 480 | 1.00 |
| 5 | 35.82% | 20.18% | 40.67% | 3.33% | 480 | 1.00 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for passivating a surface of a dehydrochlorination reactor comprising: stopping a flow of hydrochlorofluoropropane to a reactor, passing a gas mixture comprising hydrogen gas through the reactor at a temperature of at least 25° C. for a period of time sufficient to restore the selectivity of a dehydrochlorination reaction, stopping the flow of the hydrogen gas mixture, and resuming the flow of hydrochlorofluoropropane to the dehydrochlorination reaction, wherein the gas mixture further comprises an inert diluent gas, and wherein the concentration of hydrogen gas in said gas mixture is at least 0.5% by mole percent.

2. The process of claim 1, wherein the concentration of hydrogen gas in said gas mixture is at least 3% by mole percent.

3. The process of claim 1, wherein the concentration of hydrogen gas in said gas mixture is at least 10% by mole percent.

4. The process of claim 1 wherein said inert diluent gas is nitrogen, helium, argon or neon and mixtures thereof.

5. The process of claim 1, wherein the process is maintained at a pressure of at least one atmosphere.

6. The process of claim 1, wherein the reactor is maintained at a temperature of at least 200° C.

7. The process of claim 1, wherein the selectivity for dehydrochlorination is increased to at least 90%.

8. The process of claim 1, wherein the selectivity for dehydrochlorination is increased to at least 95%.

9. A process for producing a fluoropropene of formula $CF_3CX=CX_2$, wherein each X is F or H, at least one X is H and at least one X is F, comprising:
   pyrolyzing a hydrochlorofluoropropane of formula $CF_3CXYCX_2Y$, wherein each X is F or H, at least one X is H, and at least one X is F and one Y is Cl and the other Y is H, in the gas-phase in the absence of a catalyst in a reaction vessel, maintained at a temperature high enough to effect the pyrolysis of said hydrochlorofluoropropane to said fluoropropene, and wherein said reaction vessel is periodically subjected to a passivation step to passivate the inner surface of said reaction vessel, wherein said passivation step comprises
   (i) stopping the flow of hydrochlorofluoropropane to the reaction vessel, passing a gas mixture comprising hydrogen gas through the reactor at a temperature of at least 200° C. for a period of time sufficient to restore the selectivity of a dehydrochlorination reaction, stopping the flow of the gas mixture, and resuming the flow of hydrochlorofluoropropane to resume the pyrolysis reaction, or
   (ii) introducing a flow of a gas mixture comprising hydrogen gas into said reactor while the flow of hydrochlorofluoropropane is continuing, for a time sufficient to maintain the selectivity of the dehydrochlorination reaction, and then discontinuing said flow of said gas mixture comprising hydrogen
   wherein the gas mixture further comprises an inert diluent gas, and wherein the concentration of hydrogen gas in said gas mixture is at least 0.5% by mole percent.

10. The process of claim 9, wherein the inert diluent gas is nitrogen, helium, argon or neon.

11. The process of claim 9, wherein the passivation step is performed after 2000 hours of operation.

12. The process of claim 9, wherein the passivation step is performed after 50 hours of operation.

13. The process of claim 9, wherein the hydrogen gas in said gas mixture is at least 3% by mole percent.

14. The process of claim 9, wherein the selectivity of said dehydrochlorination reaction is increased to at least 90%.

15. The process of claim 9, wherein the selectivity of said dehydrochlorination reaction is increased to at least 95%.

16. The process of claim 9, wherein said passivation step (ii) is conducted at a temperature of at least 400° C.

17. A process for producing a fluoropropene of formula $CF_3CX=CX_2$, wherein each X is F or H, at least one X is H and at least one X is F, comprising:
pyrolyzing a hydrochlorofluoropropane of formula $CF_3CXYCX_2Y$, wherein each X is F or H, at least one X is H, and at least one X is F and one Y is Cl and the other Y is H, in the gas-phase in the absence of a catalyst in a reaction vessel, maintained at a temperature high enough to effect the pyrolysis of said hydrochlorofluoropropane to said fluoropropene, and wherein said hydrochlorofluoropropane comprises less than 300 ppm of hydrogen fluoride.

18. A process for passivating a surface of a dehydrochlorination reactor comprising:
stopping a flow of hydrochlorofluoropropane to a reactor,
passing a gas mixture comprising a reducing agent comprising carbon monoxide (CO) and optionally other reducing agents selected from $NH_3$, $CH_4$, hydrogen and combinations thereof, optionally mixed with one or more inert diluents, through the reactor at a temperature of at least 25° C. for a period of time sufficient to restore the selectivity of a dehydrochlorination reaction, or (ii) a reducing agent comprising $NH_3$ optionally mixed with one or more inert diluents, through the reactor at a temperature of at least 430° C. for a period of time sufficient to restore the selectivity of a dehydrochlorination reaction,
stopping the flow of the gas mixture, and
resuming the flow of hydrochlorofluoropropane to the dehydrochlorination reaction.

19. The process of claim 18 wherein the $NH_3$ is mixed with nitrogen.

20. The process of claim 1 wherein the concentration of hydrogen gas in said gas mixture is 0.5 mole percent to 30 mole percent.

21. The process of claim 20 wherein the concentration of hydrogen gas in said gas mixture is 3 mole percent to 30 mole percent.

* * * * *